US011382774B2

(12) United States Patent
Alley et al.

(10) Patent No.: US 11,382,774 B2
(45) Date of Patent: *Jul. 12, 2022

(54) METHODS FOR BONE STABILIZATION

(71) Applicant: Randall D Alley, Thousand Oaks, CA (US)

(72) Inventors: Randall D Alley, Thousand Oaks, CA (US); T. Walley Williams, III, Belmont, CA (US)

(73) Assignee: Randall D. Alley, Thousand Oaks, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/900,786

(22) Filed: Jun. 12, 2020

(65) Prior Publication Data
US 2020/0405508 A1 Dec. 31, 2020

Related U.S. Application Data

(63) Continuation of application No. 16/163,318, filed on Oct. 17, 2018, now Pat. No. 10,702,404, which is a
(Continued)

(51) Int. Cl.
A61F 2/78 (2006.01)
A61F 2/80 (2006.01)
(Continued)

(52) U.S. Cl.
CPC .............. A61F 2/78 (2013.01); A61F 2/5046 (2013.01); A61F 2/76 (2013.01); A61F 2/80 (2013.01);
(Continued)

(58) Field of Classification Search
CPC ............. A61F 2/78; A61F 2/7812; A61F 2/80
See application file for complete search history.

(56) References Cited

U.S. PATENT DOCUMENTS 2,658,388 A 11/1953 Feine
4,128,903 A 12/1978 Marsh et al.
(Continued)

FOREIGN PATENT DOCUMENTS

FR 2539616 7/1984
WO 2011035253 A1 3/2011

OTHER PUBLICATIONS

Hutter, Charles G. "A Suction Socket Prosthesis Without Suction", Orthopedic & Prosthetic Appliance Journal, Sep. 1957, pp. 39-43.
(Continued)

Primary Examiner — Marcia L Watkins
(74) Attorney, Agent, or Firm — Joseph A. Andelin; Fish IP Law, LLP

(57) ABSTRACT

A method for reducing motion of a skeletal structure in a limb towards a wall of an interface is described. The interface comprises a plurality of compression areas that are longitudinally-shaped and oriented longitudinally along the length of limb. The method comprises selecting, during a process of creating the interface, a compression level for the compression areas that compresses soft tissue against the skeletal structure. The method also comprises donning the interface over the limb to apply a plurality of compressive forces that is sufficient to aid in suspension of the interface on the limb and reduce motion of the skeletal structure toward a wall of the interface.

20 Claims, 14 Drawing Sheets

Related U.S. Application Data continuation of application No. 15/258,727, filed on Sep. 7, 2016, now Pat. No. 10,123,888, which is a continuation of application No. 13/663,282, filed on Oct. 29, 2012, now abandoned, which is a continuation of application No. 12/945,876, filed on Nov. 14, 2010, now Pat. No. 8,323,353, which is a continuation-in-part of application No. 12/792,728, filed on Jun. 2, 2010, now abandoned, which is a continuation-in-part of application No. 12/380,861, filed on Mar. 4, 2009, now abandoned.

(60) Provisional application No. 61/068,263, filed on Mar. 4, 2008.

(51) Int. Cl.
*A61F 2/50* (2006.01)
*A61F 2/76* (2006.01)
*B33Y 80/00* (2015.01)
*A61B 5/00* (2006.01)
*A61B 5/107* (2006.01)

(52) U.S. Cl.
CPC ................. *A61B 5/00* (2013.01); *A61B 5/107* (2013.01); *A61F 2002/5049* (2013.01); *A61F 2002/5053* (2013.01); *A61F 2002/5056* (2013.01); *A61F 2002/7818* (2013.01); *B33Y 80/00* (2014.12)

(56) References Cited

U.S. PATENT DOCUMENTS

| | | |
|---|---|---|
| 5,405,405 A | 4/1995 | Love |
| 5,432,703 A | 7/1995 | Clynch et al. |
| 6,077,300 A | 6/2000 | Sabolich et al. |
| 7,162,322 B2 | 1/2007 | Arbogast et al. |
| 7,239,937 B2 | 7/2007 | Slemker et al. |
| 7,356,379 B2 | 4/2008 | Slemker et al. |
| 7,817,004 B2 | 10/2010 | Fullerton et al. |
| 8,241,296 B2 | 8/2012 | Wasielewski |
| 8,443,501 B2 | 5/2013 | Mahon |
| 2003/0195636 A1 | 10/2003 | Coop |
| 2004/0030411 A1* | 2/2004 | Caspers ............... A61F 2/5046 623/37 |
| 2004/0167638 A1 | 8/2004 | Caspers |
| 2008/0147204 A1 | 6/2008 | Ezenwa |
| 2009/0271000 A1 | 10/2009 | Altobelli et al. |
| 2010/0028116 A1 | 4/2010 | Johnson et al. |
| 2010/0274364 A1 | 10/2010 | Pacanowsky et al. |
| 2011/0071647 A1 | 3/2011 | Mahon |
| 2011/0247321 A1 | 10/2011 | Streeter et al. |
| 2012/0101597 A1 | 4/2012 | Bache |
| 2013/0247353 A1 | 9/2013 | Mahon |
| 2017/0065442 A1 | 3/2017 | Alley |

OTHER PUBLICATIONS

Volkert, R., "Frame type socket for lower limb prostheses", Prosthetics and Orthotics International, 1982, 6, 88-92.

* cited by examiner

METHODS FOR BONE STABILIZATION

This application is a continuation of and claims priority from U.S. patent application Ser. No. 16/163,318, filed on Oct. 17, 2018, which is a continuation of and claims priority from U.S. patent application Ser. No. 15/258,727, filed on Sep. 7, 2016, which is a continuation of and claims priority from U.S. patent application Ser. No. 13/663,282, filed on Oct. 29, 2012, which is a continuation of and claims priority from U.S. patent application Ser. No. 12/945,876, filed on Nov. 14, 2010, which is a continuation-in-part of and claims priority from U.S. patent application Ser. No. 12/792,728, filed on Jun. 2, 2010, which is a continuation-in-part of and claims priority from U.S. patent application Ser. No. 12/380,861, filed on Mar. 4, 2009, which claims priority from U.S. Provisional Patent Application Ser. No. 61/068,263 filed Mar. 4, 2008, all incorporated by reference herein.

FIELD OF THE INVENTION

The present invention relates to the prosthetic limbs worn by upper or lower limb amputees and in particular to the portion of a limb prosthesis that is in direct contact with the user's skin.

BACKGROUND

Definitions of Terms

Socket—is that part of a prosthesis in direct contact with the user's skin. The word Socket usually implies a traditional socket that is essentially circular in cross section. A traditional prosthesis consists of an inner socket to interface with the user's skin and an outer socket over it that continues to incorporate the mechanisms that comprise the next distal structure which may be a joint or a device to function as a foot or gripping device. The inner and outer sockets may be separate structures or may be unitary consisting of a single unit.

Interface—is often used as a synonym for socket, but is more often reserved for socket-like structures that have openings in the outer socket and occasionally in both the outer and inner sockets.

Cast—is a thin layer of wet plaster impregnated gauze wrapped around a residual limb and the surrounding body parts and then permitted to harden to reproduce the shape of the limb. While the plaster is hardening, pressure from the hands of the plaster technician often modifies the shape to accommodate the underlying boney anatomy.

Positive Model—is the plaster model that results from filling a cast with plaster or similar material. Modifications by adding and subtracting plaster are made to this model before its outer surface is used to define the shape of the user's socket or interface.

Check Socket—is a temporary socket made over the model and used to test whether the modifications have had the desired effect on the fit of the resulting socket.

Channel—is used here to describe a longitudinal area where the wall of a socket is depressed inward as close to the underlying skeletal structures as is comfortable.

Relief Area—is the region in a socket system between two channels or around or near a compressed area which provides a place for the displaced tissue to migrate.

Lost Motion—is the motion of the skeletal structures with respect to the prosthetic interface when force is applied between the two as would occur as an amputee tries to move the prosthesis as a whole. In a traditional socket lost motion occurs when the bone moves toward the socket wall a substantial distance before imparting force to the wall.

Compression Bar—is a long flat bar typically a little shorter than the shaft of the remaining long bone(s). The width of the bar is usually about ten percent of the circumference of the remaining limb.

Optimal Tissue Compression—is compression of the tissue against the socket wall such that lost motion is minimized without causing discomfort to the user.

High-fidelity Interface or device—is the name given to the socket or interface that utilizes compression stabilization as the basis for its function and physical structure.

DESCRIPTION OF THE RELATED ART

Historically the prosthetic user interface has been a cylindrical socket that merely surrounds the remaining limb part with some contouring of the proximal brim so that it will accommodate the shape of the next proximal joint or body part. Typically, this socket is made by taking a plaster cast over the limb and filling it with plaster to form a positive model of the limb. Minor changes are made to this shape to relieve boney prominences. When this model is used to create a socket by laminating or thermoforming a layer of plastic there over, the resulting socket mainly encapsulates the limb part. Conventionally, no modification of the traditional model is done. This opportunity to specifically enhance the resulting structure's ability to impart desired motion to the complete prosthesis, and to prevent undesired motion from occurring, has been overlooked, even though these are the most important functions of the interface. The traditional encapsulating or closed volume socket merely contains the soft tissue but does little or nothing to prevent lost motion between the socket and the underlying skeletal structure.

Some improvements have been made in the traditional interface. In particular, many technicians replace the fully encapsulating outer socket with a frame having one or more openings. This change is accompanied by making the inner socket of a flexible material. The resulting frame-style design usually is more comfortable. New materials such as carbon fiber composites add rigidity where needed especially in open frame designs. New flexible materials allow the socket wall to flex in other areas for comfort. Even when these newer flexible materials are used, the soft liner still fully encapsulates the remaining limb as traditionally done, and thus provides a compressive or elastic force to all of the limb's soft tissue.

Conventional laminations over a plaster model work best when the surfaces of the model are convex facing outward, following the general contours of the outside surface of the limb.

SUMMARY OF THE INVENTION

In a preferred embodiment of the invention a mold (negative model) is made by making a cast of a remaining limb on which a prosthesis will be used. From the mold/cast, a positive model is made of the remaining limb. There are deep channels formed in the positive model, which are a cause of excessive thickness in these areas when conventional lamination procedures are used. Where the areas between the channels are to be left open, however, the model may be brought almost flush with the edges of the compressed areas. This alteration permits a much stronger lamination. Another technique to strengthen the resulting struts is to corrugate the compression channel area to create a resistance to flex upon lamination.

When taking a cast of the area above the knee, prosthetists are often assisted by using jigs especially to establish the shape of the brim area for transfemoral sockets. In the new socket technology of this invention one may also use a jig to assist in achieving an optimal cast of the area above the knee.

Preventing Lost Motion

In one embodiment, a basis of this invention stems from a simple observation using a procedure such as described below. A person holds his/her arm in a fixed position so that an experimenter cannot easily move the arm side to side. The experimenter then pushes with a finger on the fleshy area over the long bone of the upper arm. Typically, the finger will push into the soft tissue a centimeter or more before it compresses the tissue against the bone and no further motion is possible without the subject moving. During compression, tissue moves aside away from the area of compression. From the inventor's knowledge, no prior designs have specifically allowed for the displacement of tissue as a requirement for achieving stability even if local compressed areas exist. For a long bone to be fully stabilized with respect to the prosthetic interface, compression must be applied in a specific way. Typically three or four channels are created in the socket along the entire length of the bone except at the very ends. Accordingly, the channels extend proximate to ends of the bone, e.g. at least eighty and more preferably at least ninety percent of the existing longest bone in the existing limb. The inner surfaces of these channels compress the tissue against the long bone until little further motion is possible. For this compression to be effective, there must be a longitudinal relief area between each pair of channels. The channels and the relief areas are two key elements of a preferred embodiment of the invention and both must be present for optimal performance. In a more preferred embodiment, a third key element is that at least three channels are needed to impart full stability.

Creating the Compression Stabilized Socket Interface

The traditional prosthetic socket is created by taking a cast, making a positive model, and modifying the model to create a form for shaping a final socket interface. An important element of a preferred embodiment of this invention is the use of the traditional sequence in a new way. Three to four compression bars are made prior to taking the cast. These are tested by spacing them appropriately around the remaining limb and pushing in. Care is given to both the physical and anatomical structures of the limb in determining proper placement. In the case of the upper limb, specifically the humeral level in which positional precision and lifting capacity take precedent, the locations of these compression bars are biased toward stabilization in flexion and abduction, the two most common functional motions utilized, resulting in narrower relief windows in the anterior and lateral areas of the socket. The length, width, and curvature of the bars are adjusted until they lock the underlying bone in place when equal pressure is applied to the bars. The individual bars are checked to see if they rock end-to-end when pressure is shifted in which case a change in shape is indicated. Before taking the cast, the prosthetist must decide how to arrange the bars around the limb so that forces are optimally transmitted when the resulting interface is used. The underlying location of nerves and other structures will determine the exact angular orientation of the bars and may determine the optimum number of bars to use.

The cast is taken by applying a loose wrap of wet elastic casting plaster. The bars are then placed in the pre-planned positions, pressed into the elastic wrap and soft tissue by hand or with a casting jig with sufficient force to impart substantial compression on the limb and held in place while the plaster sets. It is important for the wrap to be able to stretch so that the displaced tissue has somewhere to go. Even in the best of circumstances, the plaster will prevent the bars from achieving optimal penetration. This is corrected during the cast rectification stage. Before, during or after the channels in the plaster and the bulges in between are sufficiently set, the proximal parts of the cast are taken in the usual manner. However, some areas in this secondary area of the wrap may also need to be compressed by the fingers of the cast taker to create additional areas of pre-compression.

For taking a femoral level cast, the distances and forces needed are greater and a bar-location jig is of great help. This jig is an integral part of the invention for femoral casting and femoral interface sockets and could also be used if desired for humeral casting. The jig consists of two or more stiff "d"- or "c"-shaped rings with the flattened surface of the d-rings or the open surface of the c-rings positioned to the medial or inside area next to the midline of the body or the opposite leg if present. These rings are large enough to allow some space inside the rings when they are placed around the limb. Each ring can accept a single screw attachment or plurality of screw attachments. Each attachment can be oriented azimuthally around the ring and then locked in place. Each attachment has a screw or screws aimed at the center of the ring capable of applying force to one of the channel-forming bars. In addition the attachments are open on one of the sides that face parallel to the limb in the d-ring design. This opening permits the prosthetist to remove a single pair of attachments and the underlying bar after the preliminary setup described below. The c-ring design inherently already has this opening. Small snap-in pockets along the outside of each bar and the fact that the screw ends are spherical prevent slipping once the bars are in place. In the ideal embodiment the pockets have a restriction at the opening that makes the attachment of the screw ends act like pop beads to hold the screw end to the bar. In a typical cast taking at the femoral level, two rings are used and each has four attachments oriented approximately ninety degrees apart. In the design utilizing two screws for each compression bar, the attachment screws are placed in pockets on the bars about twenty percent of the length of the bar in from the end. Before the cast is taken the prosthetist experiments and selects the best length and width for each bar and the optimal location. To speed application during the actual cast taking, all positions are marked with the anticipated extra circumference of the added plaster wrap accounted for.

After the cast has been filled to create a positive model, the plaster technician will usually need to deepen the channels before pulling a thermoformed check socket out of transparent plastic. If a solid-bodied check socket will be utilized, then additional plaster must be added over the relief areas of the positive model to allow sufficient displacement of soft tissue into the check socket's relief areas. Usually several check sockets will be needed. As each is applied to the user, the fit and stability of the check socket is evaluated. The color of the tissue will tell the experienced practitioner where too much compression is being applied and where there is too little. In addition substantial forces should be applied in all directions to ensure that the stabilization is optimal. Since the compression stabilized interface design requires that the areas between channels be left free or sufficiently relieved for tissue movement, there is good reason for leaving these areas fully open in the check socket unless an encapsulating or solid-body interface is desired. The user can then more readily perspire and dissipate excess body heat. With three or more long openings in the socket wall, a traditional cloth laminate is usually replaced by a stiff, strong carbon fiber reinforced laminate in the form of a frame.

Usually a temporary assembly of the distal prosthetic components is added to the final check socket and tested before the shape of the check socket is approved for creating the definitive prosthesis. For approval, the interface must transmit force and motion to the prosthesis in every direction that the user will require with minimal lost motion between the interface and the rest of the prosthesis.

In a presently preferred embodiment of the invention, there is a limb interface device. The limb interface device has either an encapsulating design with adequate soft tissue reliefs or an open cage or strut-type configuration of rigid, semi-rigid or dynamically adjustable struts appropriately contoured to a patient's residual limb. The open cage or strut-type configuration contains windows through which soft tissue can flow out of the interface confines.

The limb interface device may have any of various prosthetic components attached to it to provide an upper or lower extremity prosthesis extending from the distal end of the interface device. The regions of compression in both the encapsulating and strut-type embodiments are configured and aligned in such a way as to transfer skeletal movement as efficiently as possible such that interface response to volitional movement and interface stability are maximized. Optionally, stabilizers or other devices may be attached to a proximal end of the limb interface device.

In the open cage or strut-type configuration, the strut edges can be configured such that they are either flexible enough or shaped appropriately to mitigate edge pressure and hence soft tissue stress, or a material can be fitted to the struts such that it extends just beyond the border of the rigid or semi-rigid edge and provides a more gradual transition of pressure at this location.

In another preferred embodiment, the interface device may have the ability to alter the stiffness of the strut assembly itself on demand or automatically in response to applied loads such that edge pressure or overall strut compression is varied appropriately to prevent skin or underlying soft tissue damage. Finally, an inner, highly flexible membrane may be utilized that encapsulates the entirety of the limb and is placed between the strut assembly and the limb yet still allows sufficient soft tissue flow beyond the confines of the strut assembly such that edge pressure on the soft tissue and redundant intrinsic skeletal motion are minimized.

Although embodiments of the present interface assembly finds particular application with prosthetic limbs, it is also to be appreciated that the interface assembly may be used in other applications such as orthotics or other interface applications involving the human body.

Still other objects, advantages and constructions of the present invention, among various considered improvements and modifications, will become apparent from the detailed description provided hereinafter. It should be understood that the detailed description and specific examples, while indicating a presently preferred embodiment of the invention, are intended for purposes of illustration only and are not intended to limit the scope of the invention.

In some parts of the orthotic and prosthetic industry, cast taking has been replaced by laser scanning of the residual limb and the creation of a virtual solid model. It is anticipated that simple algorithms can be created to permit insertion of channels and bulges in a virtual model such that the area inside the virtual wall of any cross section of the residual limb would remain the same. Such an algorithm automatically creates appropriate bulges when the technician moves a portion of the wall toward the skeletal structures in the virtual model. Principles of the embodiments of the invention are not changed when the model for creating the definitive interface structure is based on a plaster cast or on a virtual model produced with software.

In a preferred embodiment, there is a prosthetic socket which prevents lost motion between an amputee's remaining limb and the prosthesis by selectively compressing tissue against the bone in some areas while providing relief in other areas so that displaced tissue is accommodated when forces are applied between the bone and the interface. Additional embodiments of the invention include methods for creating the new socket design.

It is an object of various embodiments of the present invention to provide a prosthetic interface within which the individual's upper or lower extremity residual limb part is captured with greater stability than in known prior art.

It is a further object of various embodiments of the invention to provide a mechanism to selectively compress the soft tissue between the residual limb's skeletal structure and socket structures to minimize lost motion when the skeletal structures of the residual limb move with respect to the socket and attached prosthesis.

It is a further object of various embodiments of the present invention to provide a plurality of areas of compression parallel to the long axis of the major bone or bones of the residual anatomy.

It is a further object of various embodiments of the present invention to provide open or low-compression relief areas between said areas of compression so that said compression is not impeded by the inability of the underlying tissue to flow or migrate sideways.

It is a further object of various embodiments of the present invention to provide a method for taking a cast of the residual limb that results in an approximation of the desired final shape of the socket interface.

It is a further object of various embodiments of the present invention to create areas of compression in a plaster cast parallel to the long axis of the residual limb during the process of cast taking with bulges in between that will define areas of relief in the complete prosthetic interface.

It is a further object of various embodiments of the present invention to provide check sockets where areas of relief are created by leaving the socket wall completely open or are large enough in the encapsulating version to allow for sufficient soft tissue displacement.

It is a further object of various embodiments of the present invention to provide definitive prosthetic interfaces where areas of compression, both with respect to the underlying bone as well as with respect to the area of compression just proximal to the bulging soft tissue, to stabilize the longitudinal motion of the prosthesis with respect to the skeletal anatomy thus aiding in suspension and weight bearing.

It is a further object of various embodiments of the present invention to provide definitive prosthetic sockets where a soft liner covers the limb but is stabilized by a frame there over with the frame performing the functions of a traditional outer socket. (If such a liner is used, the model over which it is formed must have bulges between the compression channels large enough to create a liner with little or no tissue compression in the areas between the areas of compression.)

It is a further object of various embodiments of the invention to provide areas into or through which a significant amount of soft tissue of the said limb can flow freely, without restriction or with minimal restriction so as to permit sufficient soft tissue flow away from areas of compression along the shaft of the bone or bones in the aforementioned areas of high compression.

It is a further object of various embodiments of the present invention to take advantage of the anatomical response such that tissue can be compressed against bone just so far before further motion is impeded if there is room for the displaced tissue to move out of the way.

It is a further object of various embodiments of the present invention to create prosthetic sockets with longitudinal grooves alternated with areas sufficiently open that the displaced tissue suffers no compression.

It is a further object of various embodiments of the present invention to create sockets that have three or more compression channels so that lost motion is prevented in all directions.

It is a further object of various embodiments of the present invention to shape the interior surfaces of the grooves such that when the prosthesis is loaded the local pressure along the length of the bone is equal without excessive pressure at the ends.

It is a further object of various embodiments of the present invention to provide means for creating a prosthetic interface by applying a plurality of bars or a loose plaster wrap during the cast taking procedure.

It is a further object of various embodiments of the present invention to provide a jig for holding the bars in position during cast taking.

It is a further object of various embodiments of the present invention to provide a jig having two or more rings larger in diameter than the limb. Each ring has a single or plurality of snap-in-place screw holder(s) with adjustment screws oriented so the axis of the screw passes through the center of the ring.

It is a further object of various embodiments of the present invention to provide screw holders that are applied to the ring by moving parallel to the axis of the ring. This feature permits a bar screw holder or a bar and two screw holders to be removed from a pair of rings as a unit.

It is a further object of various embodiments of the present invention to provide adjustment screws with spherical ends.

It is a further object of various embodiments of the present invention to provide a snap-in socket or plurality of snap-in sockets along the center line of the outside of each bar which accept the spheres on the adjustment screws.

It is a further object of various embodiments of the present invention to provide bars with center sections that telescope so bar length can be adjusted as well as to offer different length bars to be snapped in place depending on the application.

DETAILED DESCRIPTION

Figure 1:
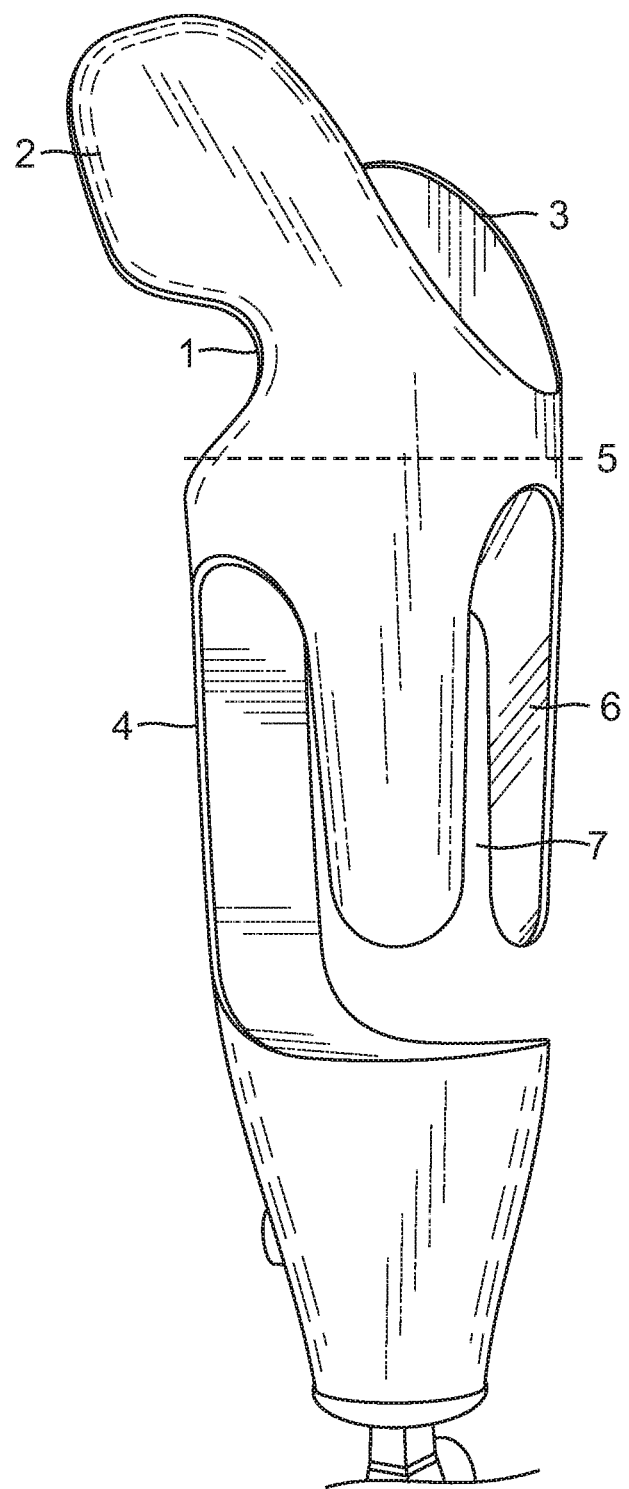
FIG. 1 is a perspective view from an anterior position of a transhumeral high-fidelity interface device in accordance with a first preferred embodiment of the invention, where the device has an open cage or strut-type structure.

As shown in FIG. 1, a the transhumeral open-cage interface embodiment, there is an upper portion 1, which has both an anterior stabilizer 2 and a posterior stabilizer 3 and which extends in a proximal (in this case toward a patient's shoulder) and medial (toward a patient's midline) direction from a lower portion 4 to stabilize the interface on a patient's body. Although stabilizers 2 and 3 are not required, they are recommended to impart or enhance rotational stability. The lower portion 4 (below line 5) has an open-cage structure. Dashed horizontal line 5 demarcates the upper and lower portions. The lower portion 4 of this open-cage embodiment has multiple, e.g. three or four struts 6, which look like fingers that extend along the long axis of the residual limb and are designed to partially encompass the residual limb, allowing soft tissue to flow through windows 7.

Figure 2:
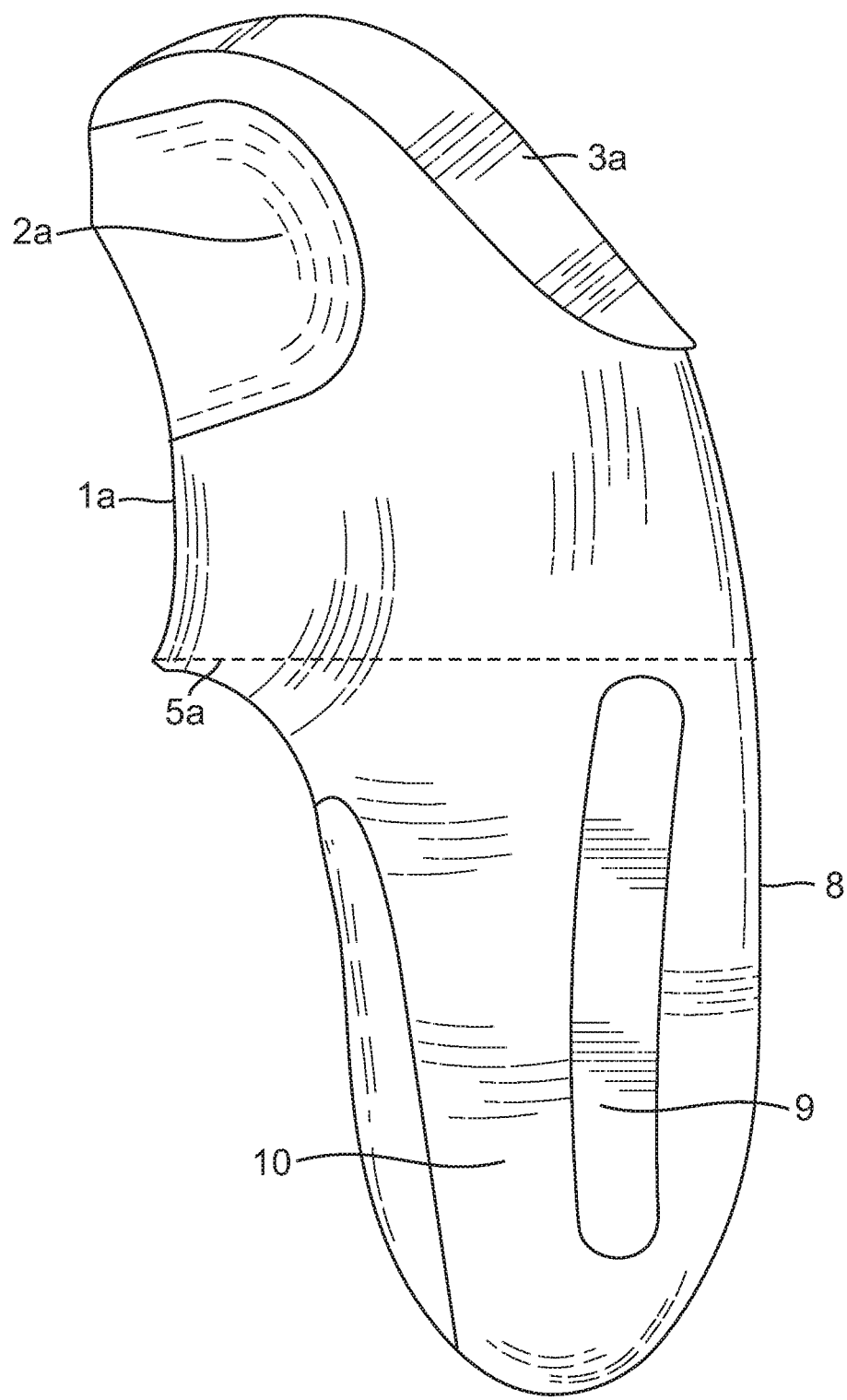
FIG. 2 is a perspective view from an anterior position of a transhumeral high-fidelity interface device in accordance with a second preferred embodiment of the invention, where the device has a closed structure.

As shown in FIG. 2, a transhumeral solid-body interface embodiment, there is an upper portion 1a, which has both an anterior stabilizer 2a and a posterior stabilizer 3a and which extends in a proximal (in this case toward the shoulder) and medial (toward the midline) direction from lower portion 8 to stabilize the interface on the body. Although stabilizers 2a and 3a are not required, they are recommended to impart or enhance rotational stability. In this embodiment, lower portion 8 is a solid body structure. A dashed horizontal line 5a demarcates the upper and lower portions. The lower portion of this solid-body embodiment has multiple, e.g. three or four, compression areas 9 and soft tissue relief areas 10 that extend along the long axis of the residual limb and are arranged circumferentially in an alternating compression-relief pattern as shown. Soft tissue relief areas 10 must have a volume sufficient to cleave displaced skin and other tissue from compression applied by compression areas 9.

Figure 3:
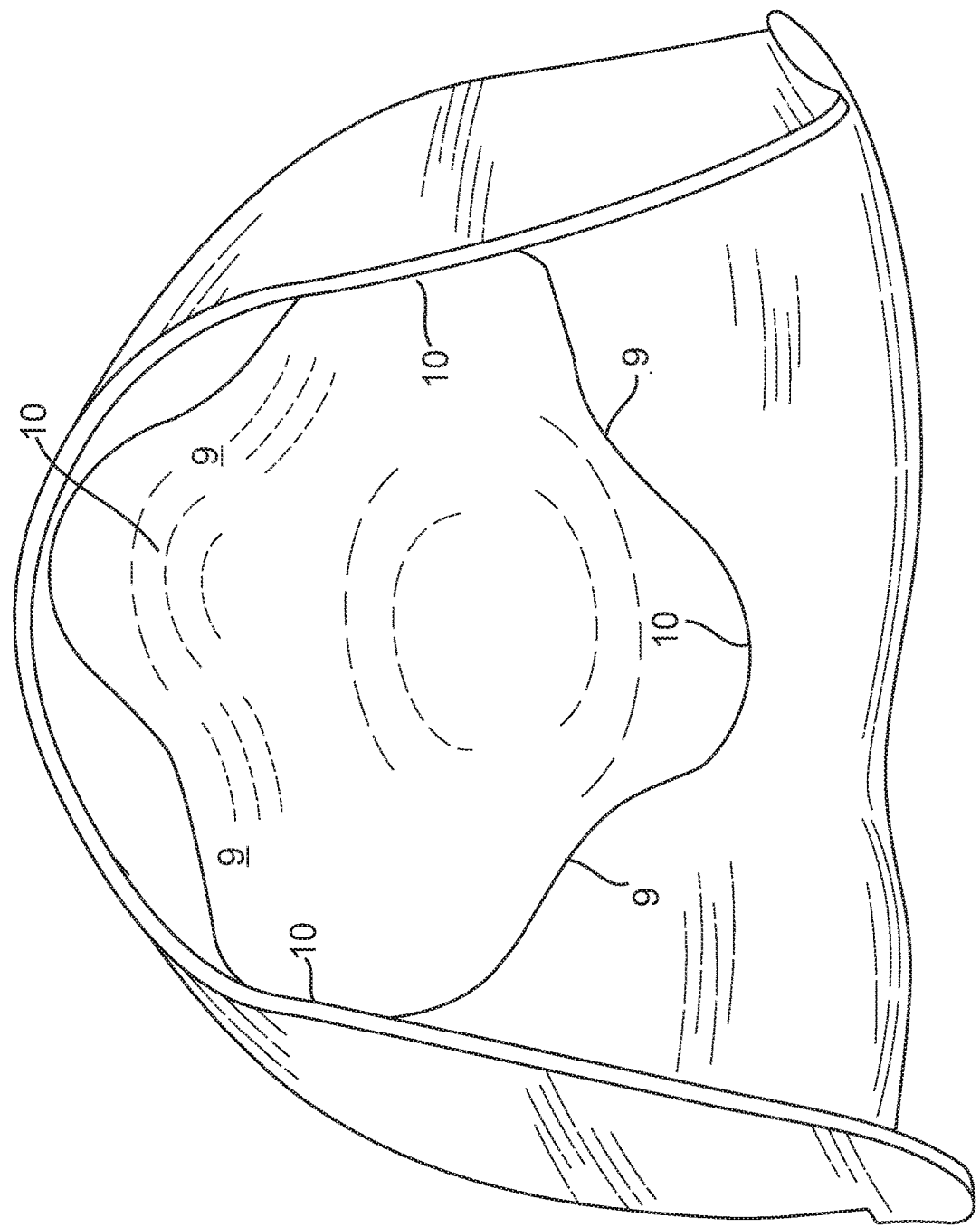
FIG. 3 is a cutaway view from the top of the interface device of FIG. 2, showing an interior thereof.

In FIG. 3, an interior of the transhumeral solid-body interface embodiment is shown, with alternating compression areas 9 and relief areas 10 indicated.

Figure 4:
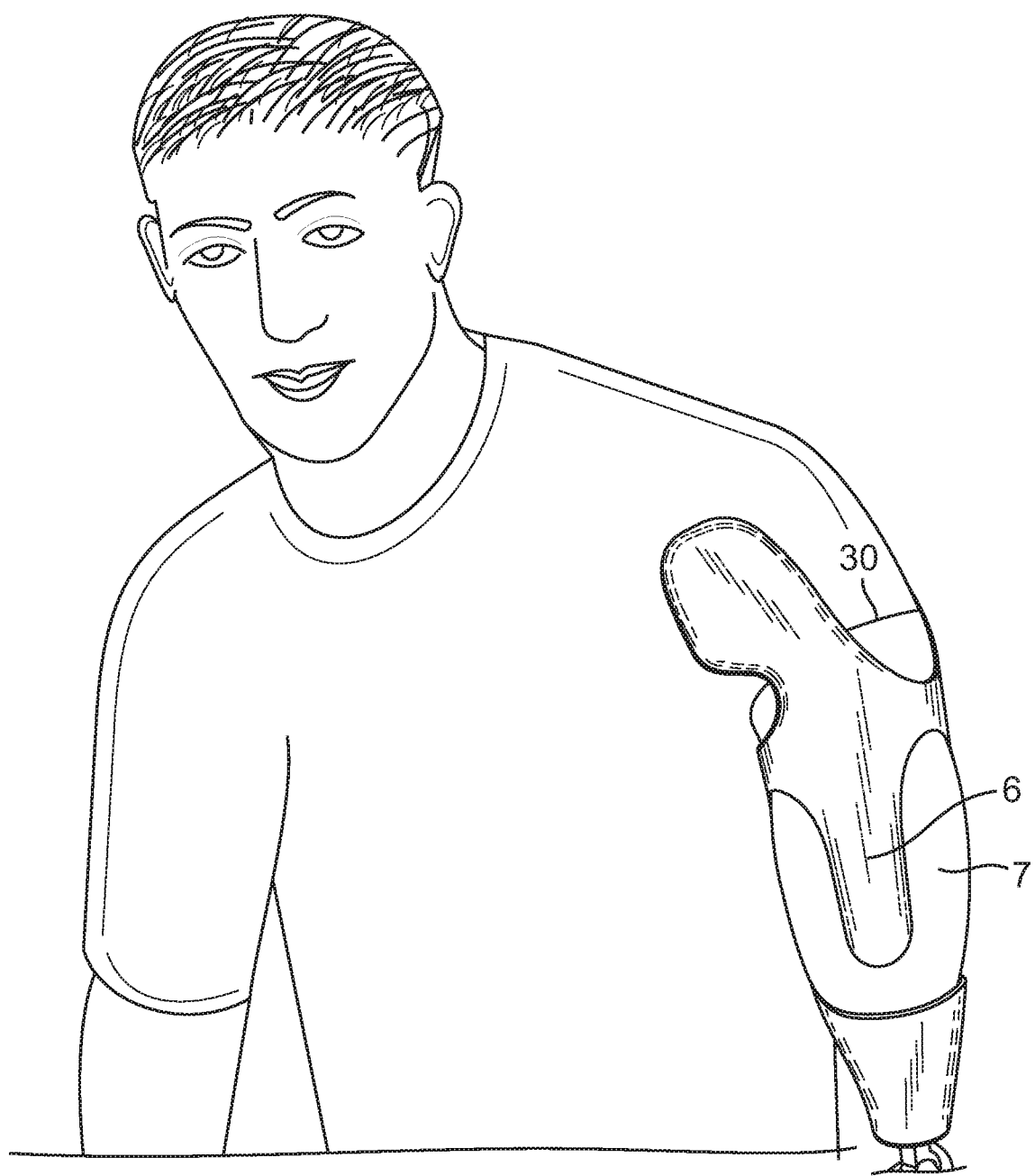
FIG. 4 is a view of the device of FIG. 1 on a patient's left arm.

In FIG. 4, a patient is shown wearing a transhumeral open-cage interface embodiment such as that of FIG. 1 with a suspension liner 30 of minimal thickness or of sufficient stretch to minimally restrict soft tissue flow through the relief windows. Struts 6 providing soft tissue compression and windows 7 allowing soft tissue flow are indicated.

Figure 5:
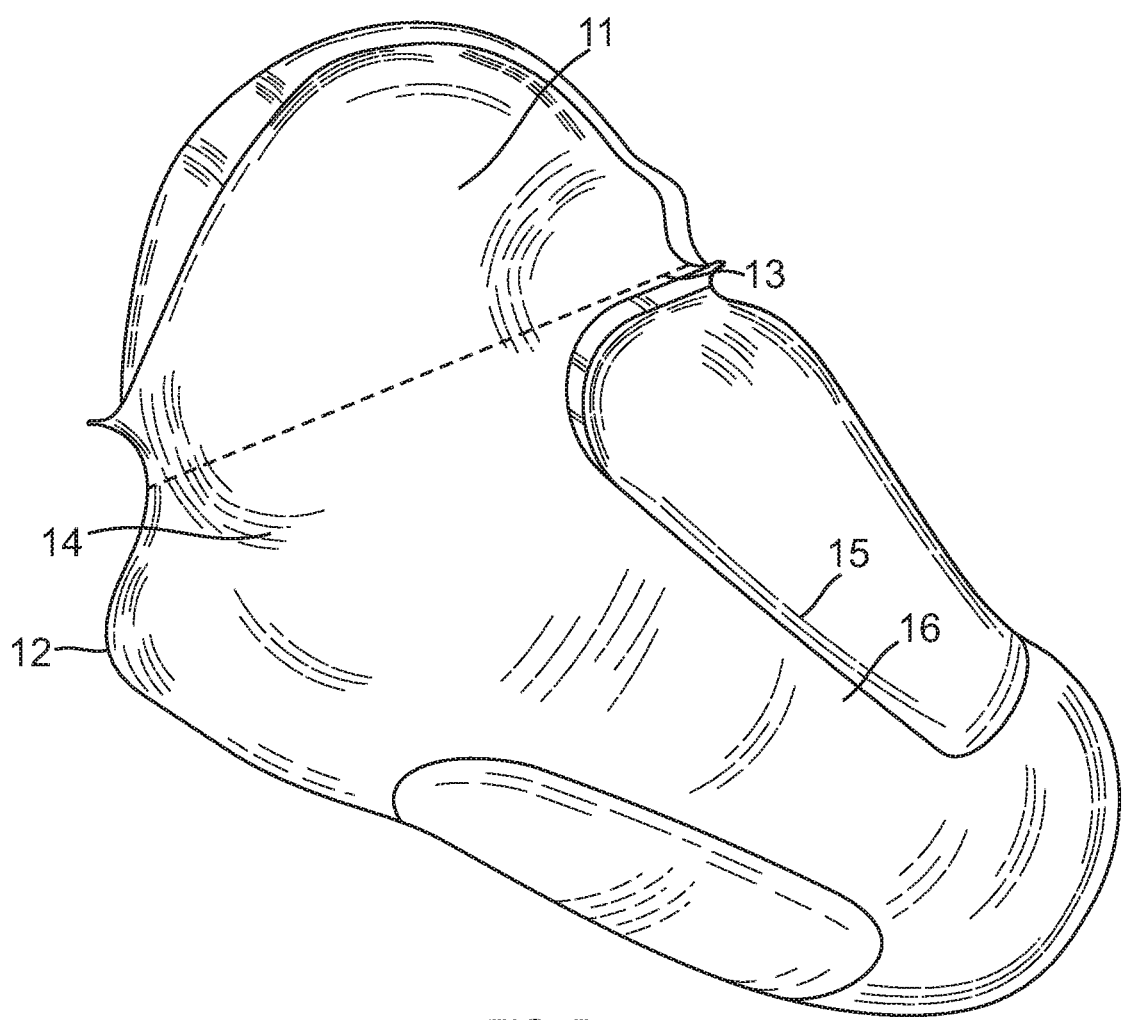
FIG. 5 is a perspective view from a medial position of a transradial high-fidelity radial interface device as a closed structure.

In FIG. 5, a transradial solid-body interface is shown. In this embodiment, there is an upper portion 11, which comprises the area of the interface proximal to olecranon 12 and cubital fold 13. A lower portion 14 has multiple, e.g. three or four, compression areas 15 and soft tissue relief areas 16 that extend along the long axis of the residual limb and are arranged circumferentially in an alternating compression-relief pattern as shown.

Figure 6:
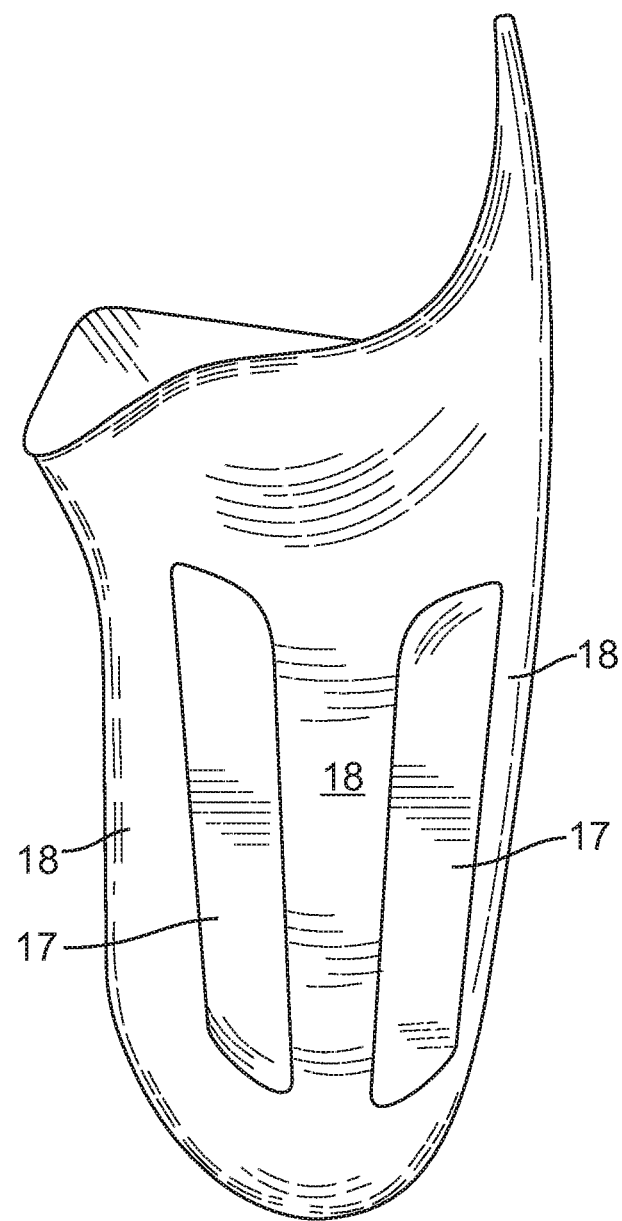
FIG. 6 is a perspective view from an anterior position of a transfemoral high-fidelity interface device in accordance with a fourth embodiment, where the device has a closed structure.

In FIG. 6, a transfemoral solid-body interface is shown. This embodiment has multiple, e.g., three or four, compression areas 17 and soft tissue relief areas 18 that extend along the long axis of the residual limb and are arranged circumferentially in an alternating compression-relief pattern as shown.

Figure 7A:
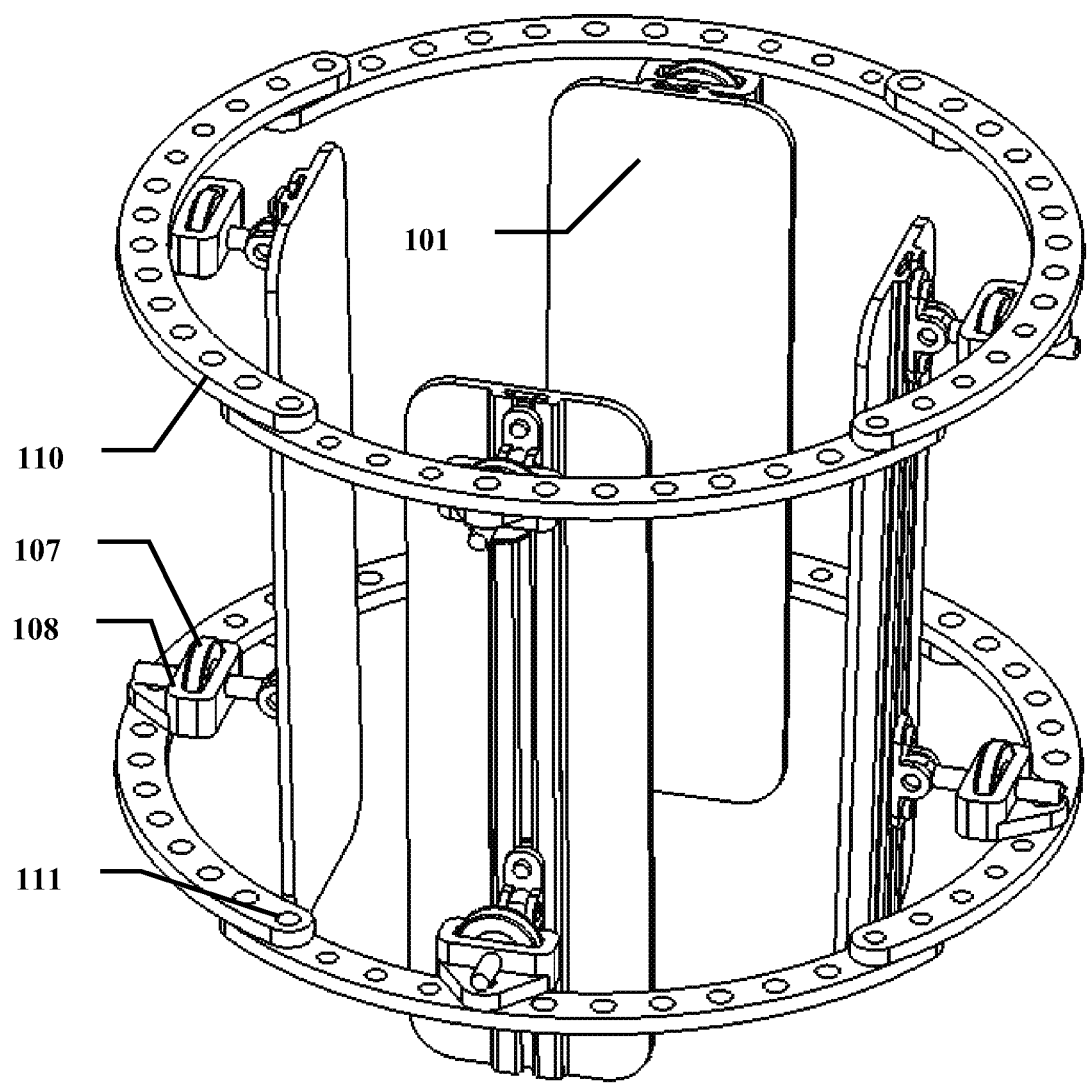
FIGS. 7a, 7b show an example of a jig design utilized for transfemoral cast taking in preparation for the creation of a transfemoral high-fidelity interface.
Figure 7B:
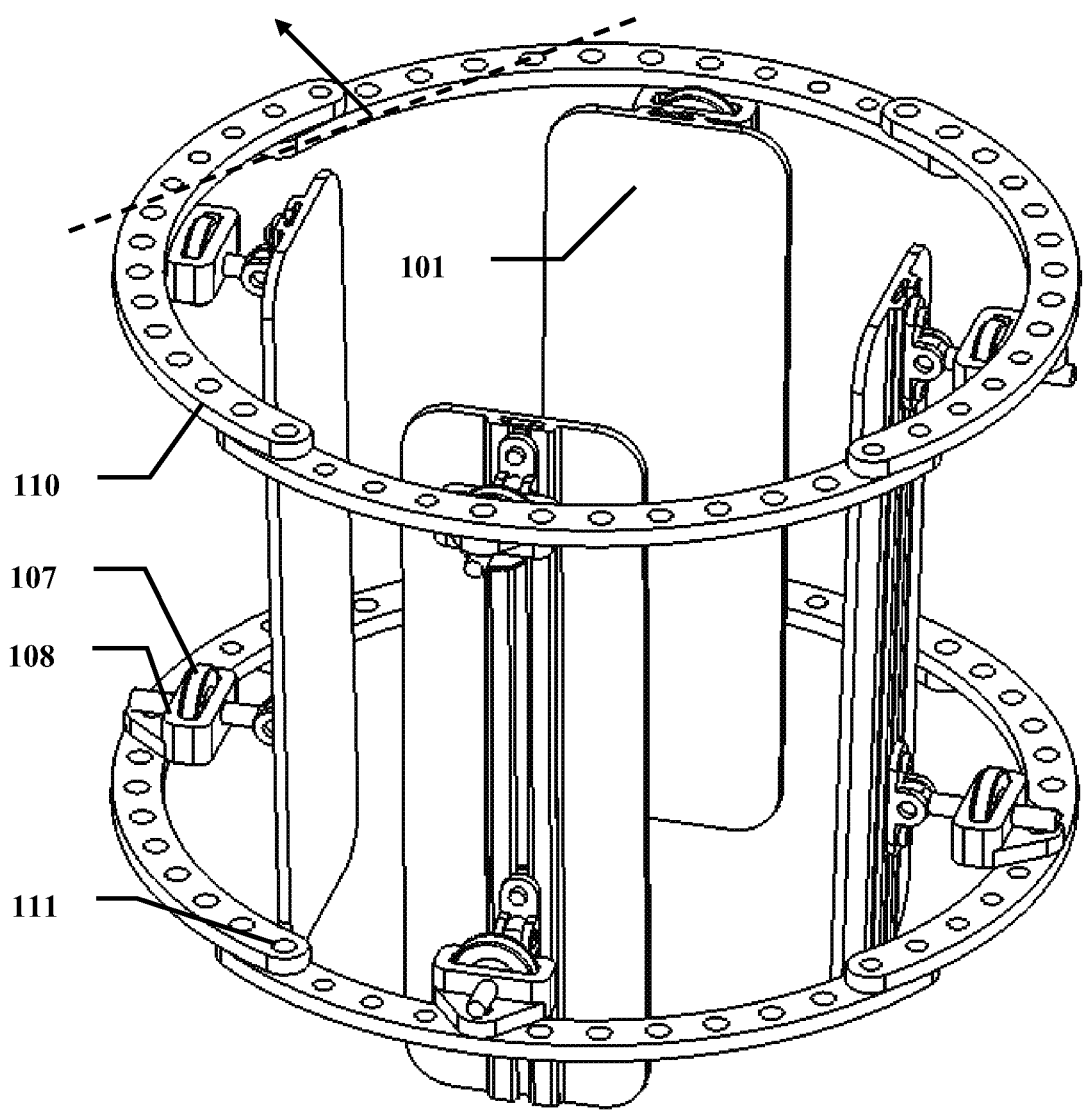

In FIGS. 7a and 7b, there is shown a tool for use in imaging (and particularly helpful for the lower limb), which tool optionally may be used with various embodiments of the invention. Imaging is a process to render a model of the limb using plaster bandage, laser scanning or other such technique. Imaging of a limb under compression may be done to create the model. This tool is essentially a connected set of adjustable bars attached to screws which in turn are connected to a circumferential or partially circumferential ring that allows this tool to be placed over the limb either before, during or after the imaging process and that applies the appropriate compression to the soft tissues of the limb in desired target areas while allowing redundant soft tissue to flow through the areas between the struts unhindered.

More specifically, the jig consists of a multiplicity of paddles 101 for pushing inward against the limb remnant of an amputee. For most purposes, four paddles preferably are used. For the configuration shown, eight sectors 110 are assembled into two rings. Eight screws are used at locations 111 to assemble the rings.

In FIG. 7b, a screw (not shown) is inserted into clearance hole 112 to secure the turnbuckle holder 108 to the sector 110. Until the screw is tight, the holder is free to rotate with respect to the sector. The turnbuckle rod 106 is threaded with an eyelet 113 on the far end to connect to paddle holder 105. A pin attaching these two parts is inserted into hole 114. Paddles 101 each have a channel 103 into which a slider 102 is captured. This slider has two threaded bosses 104 which are secured to paddle holder 105 by nuts (not shown). By loosening these two nuts the slider may be repositioned along the paddle.

To adjust the position of the paddle, a threaded wheel 107 is turned. In the configuration shown, there are a total of eight turnbuckle assemblies to position the paddles in contact with the amputee's limb. Preferably, the paddles are made from a rigid, inexpensive plastic that can be trimmed to a width and length suitable to the individual amputee fitting. All of the other components are preferably reusable.

Figure 8A:
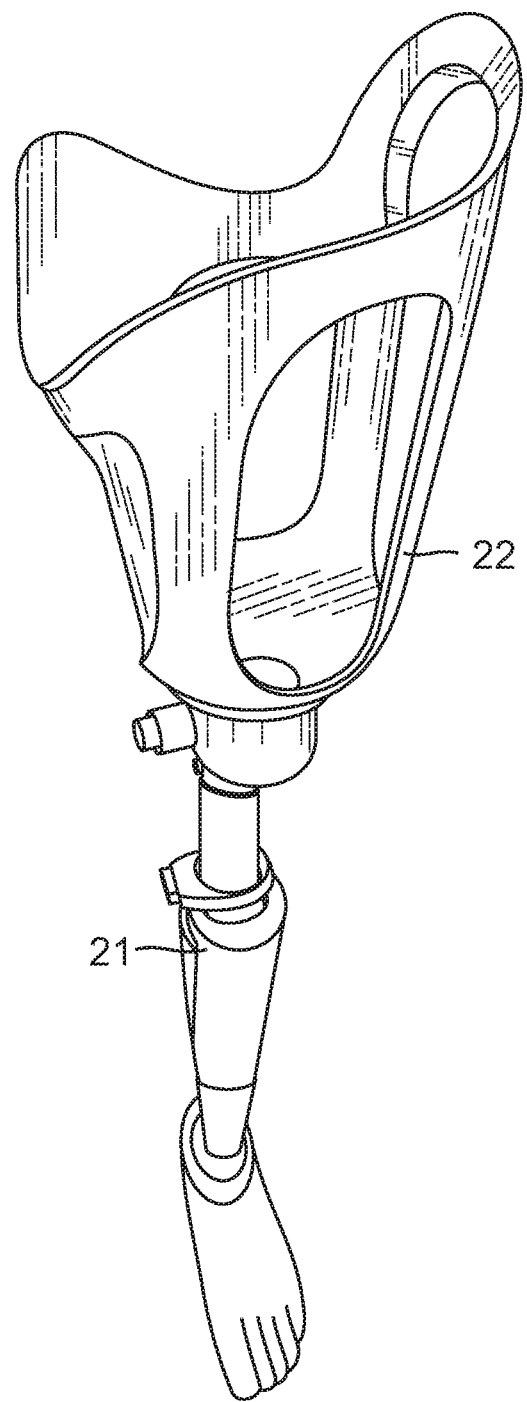
FIGS. 8a, 8b show the anterior and posterior perspectives of an exemplary transfemoral high-fidelity interface attached to prosthetic components.
Figure 8B:
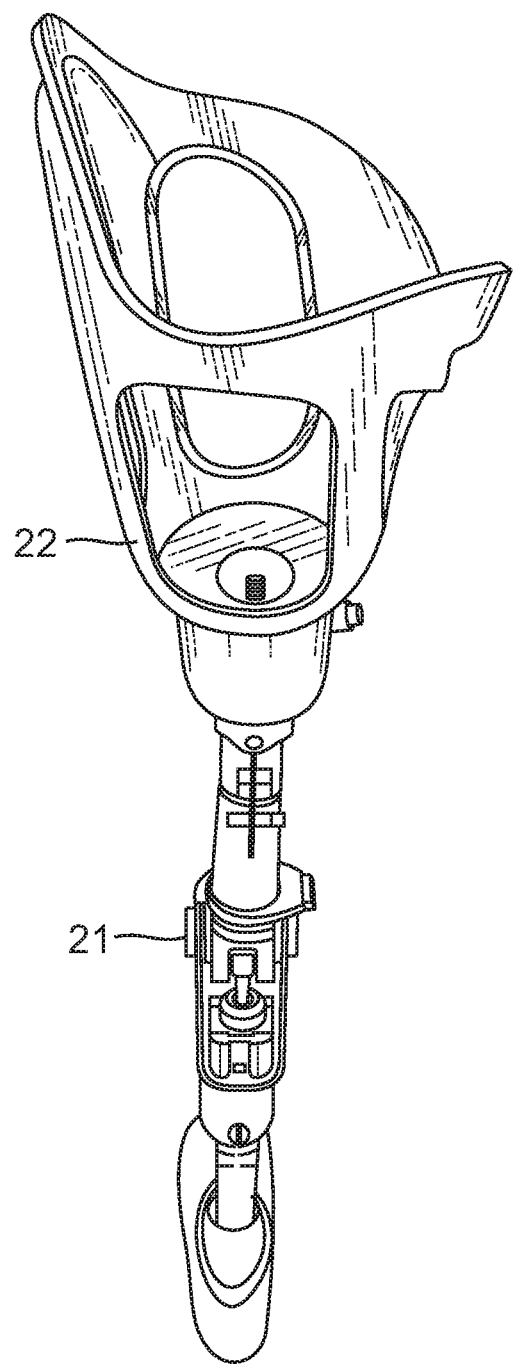

As shown in FIGS. 8a (an anterior perspective) and 8b (a posterior perspective), an exemplary prosthetic component set 22 is attached to one device 23. Various prosthetic components may be attached to the device by any one of various methods currently available or available in the future. The device may have at a proximal end any one of various support structures known in the art or developed in the future.

In a method in accordance with an embodiment of the invention, an interface device with open-cage or strut-type is fitted onto a person.

First, it is determined whether a patient needs a transradial (radial level) device, a transhumeral (humeral level) device, a transtibial (tibial level) device or a transfemoral (femoral level) device. The patient or prosthetist may select a closed device or an open cage strut-type high-fidelity device.

Second, the patient's limb radius is determined at one or more locations. Third, the device is essentially crimped during modification or creation of the device until sufficient compression from the at rest radius of the patient's limb at the cage or strut region of the device is at a desired amount. The desired amount of compression will depend in part on the patient's bone size, body fat, and other tissue parameters at the area of the cage or strut. The compression generally is at least 20% or at least 30% from the at rest radius of the limb. Typically, compression will be from 20% to 70% or 30% to 70%. The amount of compression is sufficient such that there is minimum redundant tissue between the maximum point of compression and the target bone contained within the interface such that motion capture of the bone is maximized while retaining sufficient comfort to allow the wearer to withstand the compression for a useable amount of time and to ensure adequate blood flow over time, which can be ascertained through the use of a blood perfusion sensor and monitor. The blood perfusion sensor can be utilized during casting, diagnostic interface assessment or in the definitive socket.

However, compression can be lower than 20% or higher than 70% depending upon bone size, body fat and other tissue parameters, and the prosthetist and/or physician will use the blood perfusion sensor and monitor and make a determination of the safety and effectiveness of the particular amount of compression for the particular patient.

Fourth, the modified or rectified high-fidelity device with an inner radius or inner radii of size that can be fit over the distal (free) end of the patient's limb (for fitting with a prosthesis) is selected, and applied to the patient's limb, e.g., by sliding onto the limb.

Creation and Fabrication of High-Fidelity Interface

In a method in accordance with an embodiment of the invention, an interface device with open-cage (strut-type) or solid-body configuration is fitted onto a person.

First, it is determined whether a patient needs a wrist disarticulation device, a transradial device, a transhumeral device, a symes device, a transtibial device, a knee disarticulation device, a transfemoral device or a hip disarticulation device. The patient or prosthetist may select a closed or open cage strut-type high-fidelity device as disclosed herein.

Second, the patient's limb radius is determined at one or more locations along the limb where the interface device will be fit.

Third, the interface is created using one of several different methods, all of which require modification by the prosthetist to complete fitting of such a final socket.

One method commonly employed is to cast the patient's limb utilizing a plaster bandage. This casting allows the prosthetist or clinician to add compression forces to the plaster wrap and hence to the limb in the target areas that will hold this compression and allow for subsequent tissue relief between these compression areas as the plaster sets.

The cast, which will function as a negative model or mold, is removed and filled with liquid plaster.

The liquid plaster is allowed to set in the mold.

Once the liquid plaster has solidified, the plaster bandage (mold) surrounding the solid (positive) model is removed. The positive model is now revealed to which the prosthetist or clinician applies additional compression to the target areas by carving directly on the model. Carving on the positive model creates a pressure or compression point on the target areas because the "negative" model (the socket being molded from the positive model) will now have a larger inwardly facing compression area.

Another way to generate the limb shape to be modified is to use a scanner to obtain the image shape and then modify the digital image accordingly using well known software, e.g., on a computer such as a laptop. This digital model (as modified to apply targeted compression and relief) can then be sent to a carver or 3d printer to generate a physical positive model over which a negative model (mold) can be created for fitting or additional fabrication.

In order to determine appropriate compression levels, the device is essentially crimped during modification or creation of the device until sufficient compression from the at rest radius of the patient's limb at the cage or strut region of the device is at a desired amount. The desired amount of compression will depend in part on the patient's bone size, body fat, and other tissue parameters at the area of the cage or strut. The compression generally is at least 20% from the at rest radius of the limb. Typically, compression will be from 20% to 70%, or at least 30% to 70%. For certain patients, such as very muscular, or those having calcification, the minimum compression to achieve the advantages of the inventive method may be a little below the above minimum ranges, and for certain patients, such as obese patients or others with extremely fleshy skin, a higher than 70% compression may be appropriate. However, comfort and medical safety can dictate the final appropriate amount of compression for any particular patient.

The amount of compression is sufficient such that there is minimum redundant tissue between the maximum point of compression and the target bone contained within the interface such that motion capture of the bone is maximized while retaining sufficient comfort to allow the wearer to withstand the compression for a useable amount of time.

Fourth, the decision is made whether a diagnostic interface (transparent thermoplastic socket for analysis of fit and function prior to creating the definitive model) or a definitive interface, typically consisting of a laminated framework, is to be created.

Over the now modified or crimped model, in order to create the diagnostic interface, a thermoplastic material is heated and draped or blister-formed, preferably under vacuum, to render a new negative model. Once the thermoplastic has cooled and become rigid, the plaster is then removed from within the thermoplastic interface and the interface is trimmed and smoothed and is of sufficient stiffness and transparency to allow the clinician to don it on the patient and judge the fit and pressures acting on the limb. This model can be removed from the patient's limb and trimmed or heated to change its boundaries or perimeter and shape, including the amount of compression or relief that is applied to the limb based on what is observed and comments from the wearer.

In order to create the definitive interface, an acrylic laminate (with or without stiffeners such as carbon fiber, Kevlar®, i.e., para-aramid synthetic fiber, etc.) or similar can be vacuum formed directly over the model or in the case of a frame style interface with a flexible liner and rigid frame, over an inner flexible liner that has been previously vacuum-formed over the same model.

The now compressed negative socket, whether in diagnostic or definitive form can be donned by either a push-in or pull-in method, with the latter being preferred due to the high levels of compression applied to the limb. This compression imparts friction on the skin during donning and hence makes it more difficult to get all the limb tissue down in the interface unless a donning sock or similar is used to pull the tissue in. The pull-in method utilizes a donning sock or similar such device that surrounds the limb and is pulled through a distal aperture at the distal end or bottom of the interface. As the wearer pulls down on the end of the donning sock and pulls it through the aperture, the limb is pulled down into the interface until fully seated.

Figure 9:
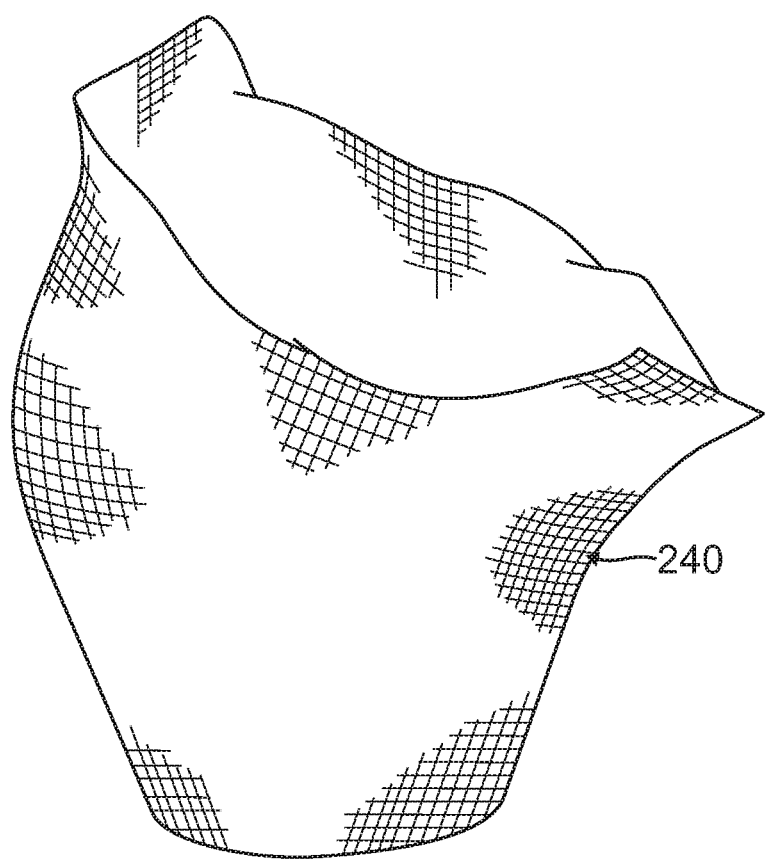
FIG. 9 is a drawing showing a casting

In FIG. 9, an example of a casting 240, e.g., for an upper limb, is shown.

Figure 10:
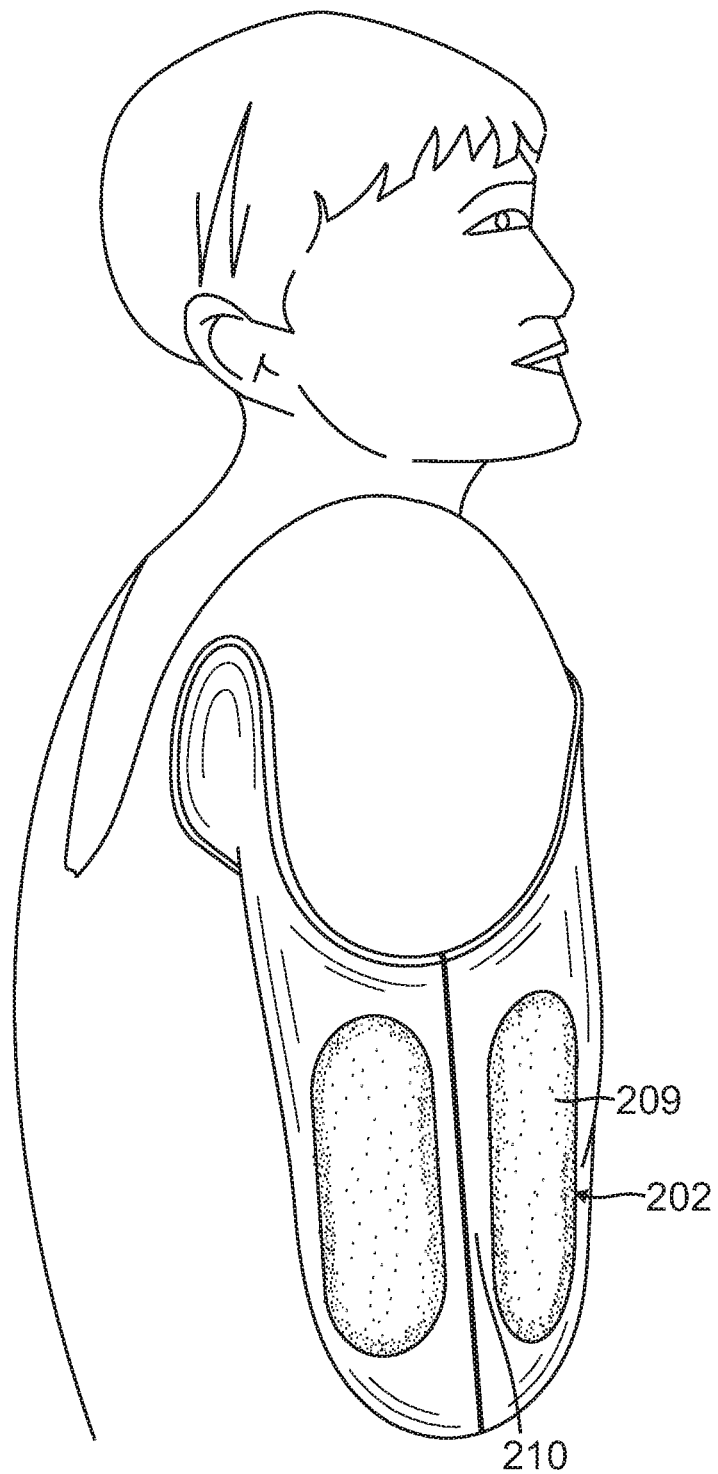
FIG. 10 is a drawing showing a mold formed from the casting.

In FIG. 10, a socket 202 having compression regions 209 and relief regions 210 is shown on a patient's limb, e.g., an upper limb.

Figure 11:
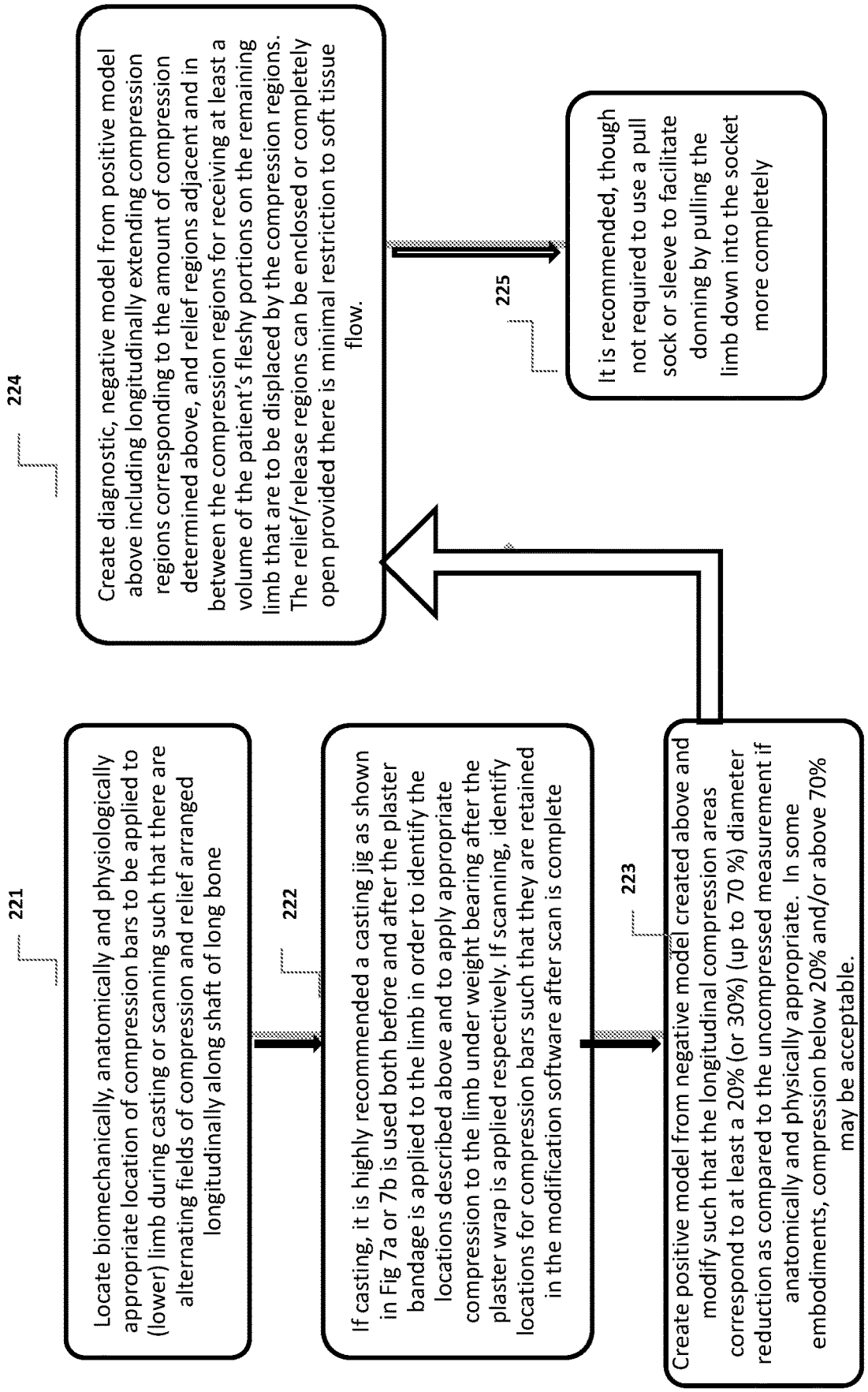
FIG. 11 is a flow chart showing steps in a process of an embodiment of the invention for making a high-fidelity interface for a prosthesis and limb, preferably a lower limb.
Figure 12:
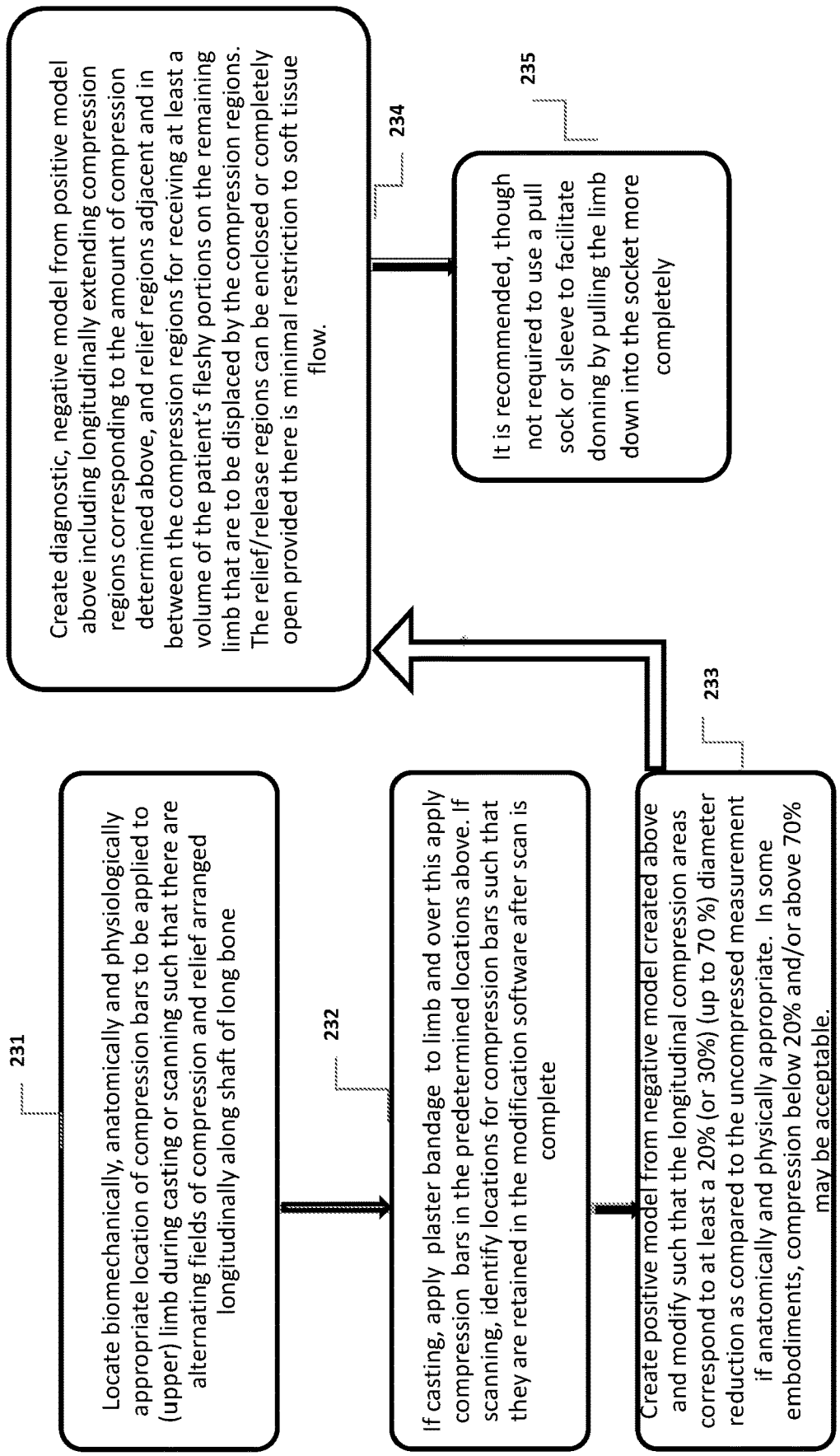
FIG. 12 is a flow chart showing steps in an alternate process of another embodiment of the invention for making a high-fidelity interface for a prosthesis and limb, preferably an upper limb.

FIG. 11 is a flow chart showing steps in a process of an embodiment of the invention for making a high-fidelity interface for a prosthesis and limb, preferably a lower limb, the lower limbs being the ones that will be bearing weight of the wearer's body; and FIG. 12 is a flow chart showing steps in an alternate process of another embodiment of the invention for making a high-fidelity interface for a prosthesis and limb, preferably an upper limb.

In FIG. 11, in a step 221, a technician will locate biomechanically, anatomically and physiologically appropriate location of compression bars to be applied to an upper limb during casting or scanning such that there are alternating fields of compression and relief arranged longitudinally along shaft of long bone.

In step 222, a technician will, if casting, preferably use a casting jig as shown in FIG. 7a or 7b both before and after the plaster bandage is applied to the limb in order to identify the locations described above and to apply appropriate compression to the limb underweight bearing conditions after the plaster wrap is applied respectively. If scanning, the technician will identify locations for compression bars such that they are retained in the modification software after scan is complete.

In step 223, a technician will create positive model from negative model created above and modify such that the longitudinal compression areas correspond to at least a 20% (or 30%) (up to 70%) diameter reduction as compared to the uncompressed measurement if anatomically and physically appropriate. In some cases, compression below 20% or above 70% may be acceptable.

In step 224, a technician will create a diagnostic, negative model from the positive model above including longitudinally extending compression regions corresponding to the amount of compression determined above, and relief regions adjacent and in between the compression regions for receiving at least a volume of the patient's fleshy portions on the remaining limb that are to be displaced by the compression regions. The relief/release regions can be enclosed or completely open provided there is minimal restriction to soft tissue flow.

In step 225, which is optional, one preferably will put on al sock or sleeve to facilitate donning by pulling the limb down into the socket more completely.

In the process of FIG. 12, in step 231, a technician will locate biomechanically, anatomically and physiologically appropriate location of compression bars to be applied to (lower) limb during casting or scanning such that there are alternating fields of compression and relief arranged longitudinally along shaft of long bone.

In step 232, the technician will, if casting, apply a plaster bandage to limb and over this apply compression bars in the predetermined locations above. If scanning, the technician will identify locations for compression bars such that they are retained in the modification software after scan is complete.

In step 233, the technician will, create positive model from negative model created above and modify such that the longitudinal compression areas correspond to at least a 20% (or 30%) (up to 70%) diameter reduction as compared to the uncompressed measurement if anatomically and physically appropriate. In some cases, compression below 20% or above 70% may be acceptable.

In step 234, the technician will create a diagnostic, negative model from the positive model above including longitudinally extending compression regions corresponding to the amount of compression determined above, and relief regions adjacent and in between the compression regions for receiving at least a volume of the patient's fleshy portions on the remaining limb that are to be displaced by the compression regions. The relief/release regions can be enclosed or completely open provided there is minimal restriction to soft tissue flow.

In step 235, which is optional, one preferably will put on al sock or sleeve to facilitate donning by pulling the limb down into the socket more completely.

Although the invention has been described using specific terms, devices, and/or methods, such description is for illustrative purposes of the preferred embodiment(s) only. Changes may be made to the preferred embodiment(s) by those of ordinary skill in the art without departing from the scope of the present invention, which is set forth in the following claims. In addition, it should be understood that aspects of the preferred embodiment(s) generally may be interchanged in whole or in part.

What is claimed is:

1. A method for reducing motion of a skeletal structure in a limb towards a wall of an interface worn on the limb, wherein the interface comprises a plurality of compression areas, the method comprising:
   selecting a compression level for each of the plurality of compression areas that compresses soft tissue of the limb against the skeletal structure when the interface is worn on the limb;
   wherein the plurality of compression areas comprises three or more longitudinally-shaped areas that are oriented longitudinally along the limb and circumferentially and equally spaced around the limb;
   wherein each of the plurality of compression areas comprises a rigid material;
   donning the interface over the limb so that the plurality of compression areas applies a plurality of compressive forces to the limb;
   wherein the plurality of compressive forces is sufficient to aid in suspension of the interface on the limb and reduce motion of the skeletal structure toward the wall of the interface throughout use thereof.

2. The method of claim 1, wherein the interface further comprises a plurality of open or low-compression relief areas, and wherein the plurality of compression areas and the plurality of relief areas are arranged in an alternating pattern.

3. The method of claim 1, wherein the interface has a closed structure.

4. The method of claim 1, wherein the interface has a strut-type configuration.

5. The method of claim 1, further comprising a step of donning an inner flexible membrane on the limb.

6. The method of claim 5, wherein the inner flexible membrane comprises a liner.

7. The method of claim 5, wherein the inner flexible membrane is donned on the limb prior to donning the interface.

8. The method of claim 5, wherein the inner flexible membrane provides an elastic force to the soft tissue.

9. The method of claim 1, wherein the step of selecting the compression level for each of the plurality of compression areas comprises determining a comfort level of the user.

10. The method of claim 9, wherein the step of determining the comfort level of the user comprises using a sensor.

11. The method of claim 1, wherein the step of selecting the compression level for each of the plurality of compression areas depends at least in part on body fat content of the limb.

12. The method of claim 1, wherein the plurality of compressive forces is sufficient such that redundant skeletal motion is minimized while retaining sufficient comfort to allow the user to withstand the compressive forces for a useable amount of time.

13. The method of claim 12, wherein the plurality of compressive forces allows adequate blood flow in the soft tissue for the useable amount of time.

14. The method of claim 1, wherein the step of selecting the compression level for each of the plurality of compression areas comprises ascertaining blood perfusion of the soft tissue using a sensor.

15. The method of claim 1, wherein the step of selecting the compression level for each of the plurality of compression areas comprises measuring an uncompressed diameter of the limb.

16. The method of claim 15, wherein, when the interface is donned, the plurality of compressive forces reduces an uncompressed diameter of the limb by at least 20%.

17. The method of claim 1, wherein the process of creating the interface comprises scanning the limb to create a digital image of the limb and modifying the digital image to apply the plurality of compression areas to create a digital model.

18. The method of claim 17, further comprising the step of creating the interface by applying the plurality of compressive forces prior to scanning the limb.

19. The method of claim 17, further comprising a step of sending the digital model to a carver or 3D printer to generate a physical model.

20. A method for reducing motion of a skeletal structure in a limb towards a wall of an interface worn on the limb, wherein the interface comprises a plurality of compression areas, the method comprising:
   selecting a compression level for each of the plurality of compression areas that compresses soft tissue of the limb against the skeletal structure when the interface is worn on the limb;
   wherein the plurality of compression areas comprises four longitudinally-shaped areas that are oriented longitudinally along the limb and spaced circumferentially around the limb at approximately ninety degrees apart;
   wherein each of the plurality of compression areas comprises a rigid material;

donning the interface over the limb so that the plurality of compression areas applies a plurality of compressive forces to the limb;

wherein the plurality of compressive forces is sufficient to aid in suspension of the interface on the limb and reduce motion of the skeletal structure toward the wall of the interface throughout use thereof.

\* \* \* \* \*